US009132418B2

(12) United States Patent
Shen et al.

(10) Patent No.: US 9,132,418 B2
(45) Date of Patent: Sep. 15, 2015

(54) MANGANESE OXIDE-STABILIZED ZIRCONIA CATALYST SUPPORT MATERIALS

(71) Applicant: CLARIANT CORPORATION, Louisville, KY (US)

(72) Inventors: Wenqin Shen, Louisville, KY (US); Franz G. Petzold, Louisville, KY (US); Karen Libby, Louisville, KY (US); Wayne Turbeville, Crestwood, KY (US)

(73) Assignee: CLARIANT CORPORATION, Louisville, KY (US)

( * ) Notice: Subject to any disclaimer, the term of this patent is extended or adjusted under 35 U.S.C. 154(b) by 0 days.

(21) Appl. No.: 14/306,332

(22) Filed: Jun. 17, 2014

(65) Prior Publication Data

US 2015/0031923 A1    Jan. 29, 2015

Related U.S. Application Data

(60) Provisional application No. 61/840,038, filed on Jul. 26, 2013.

(51) Int. Cl.

| *C07C 29/00* | (2006.01) |
| *B01J 21/00* | (2006.01) |
| *B01J 23/889* | (2006.01) |
| *B01J 37/03* | (2006.01) |
| *B01J 37/08* | (2006.01) |
| *B01J 21/06* | (2006.01) |
| *B01J 23/34* | (2006.01) |
| *B01J 23/46* | (2006.01) |
| *B01J 23/72* | (2006.01) |
| *B01J 23/755* | (2006.01) |
| *B01J 23/843* | (2006.01) |
| *B01J 35/00* | (2006.01) |
| *B01J 35/10* | (2006.01) |
| *C12P 19/02* | (2006.01) |
| *B01J 23/656* | (2006.01) |
| *C07C 29/17* | (2006.01) |
| *C07C 29/60* | (2006.01) |
| *C07C 29/132* | (2006.01) |
| *C07C 29/149* | (2006.01) |

(52) U.S. Cl.
CPC ............ *B01J 23/8892* (2013.01); *B01J 21/066* (2013.01); *B01J 23/34* (2013.01); *B01J 23/462* (2013.01); *B01J 23/6562* (2013.01); *B01J 23/72* (2013.01); *B01J 23/755* (2013.01); *B01J 23/8435* (2013.01); *B01J 35/002* (2013.01); *B01J 35/1014* (2013.01); *B01J 35/1019* (2013.01); *B01J 35/1038* (2013.01); *B01J 37/031* (2013.01); *B01J 37/08* (2013.01); *C07C 29/00* (2013.01); *C07C 29/132* (2013.01); *C07C 29/149* (2013.01); *C07C 29/172* (2013.01); *C07C 29/60* (2013.01); *C12P 19/02* (2013.01)

(58) Field of Classification Search
CPC ...... C07C 29/00; C07C 31/225; B01J 21/066; B01J 35/04
USPC .......... 568/861, 863, 881, 903; 502/324, 325, 502/439
See application file for complete search history.

(56) References Cited

U.S. PATENT DOCUMENTS

| 4,430,207 A | 2/1984 | Kukes |
| 5,217,938 A | 6/1993 | Reinalda et al. |
| 5,391,362 A | 2/1995 | Reinalda et al. |
| 5,770,541 A | 6/1998 | Vanderspurt |
| 6,034,029 A | 3/2000 | Wulff-Doring et al. |
| 6,716,886 B2 | 4/2004 | Krylova et al. |
| 6,770,251 B2 | 8/2004 | Yoshikawa |
| 6,900,361 B2 | 5/2005 | Elliott |
| 6,982,328 B2 | 1/2006 | Werpy et al. |
| 7,090,789 B2 | 8/2006 | Schiodt |
| 7,465,690 B2 | 12/2008 | Yan |
| 7,598,295 B2 | 10/2009 | Bromfield et al. |
| 7,704,483 B2 | 4/2010 | Shen et al. |
| 8,057,767 B1 | 11/2011 | Qi |
| 2004/0179994 A1 | 9/2004 | Fenouil et al. |
| 2007/0036710 A1 | 2/2007 | Fenouil et al. |
| 2009/0305882 A1 | 12/2009 | Dahar et al. |
| 2011/0301021 A1 | 12/2011 | Liu et al. |
| 2011/0319672 A1 | 12/2011 | Liu et al. |
| 2014/0249334 A1 | 9/2014 | Miller et al. |

FOREIGN PATENT DOCUMENTS

| CN | 102029166 | 4/2011 |
| RU | 2402379 | 10/2010 |
| WO | 2012171656 | 12/2012 |

OTHER PUBLICATIONS

Xiaoxiang Han "Selective hydrogenation of cinnamaldehyde over Pt/ZrO2 Catalyst modified by Cr, Mn, Fe, Co and Ni" Catalysis Letters 109 (3-4), Jul. 2006, p. 157-161.

(Continued)

*Primary Examiner* — Sikarl Witherspoon

(57) ABSTRACT

The present disclosure relates generally to catalyst support materials, catalysts and methods for using them, such as methods for converting sugars, sugar alcohols, glycerol, and bio-renewable organic acids to commercially-valuable chemicals and intermediates. One aspect of the invention is catalyst support material including $ZrO_2$ and one or more oxides of manganese ($MnO_x$), the catalyst support material being at least about 50 wt % $ZrO_2$ and $MnO_x$. In certain embodiments, the weight ratio of $ZrO_2$ to $MnO_x$ is within the range of about 1:1 to about 30:1; and/or the catalyst support material is substantially free of any binder, extrusion aid or additional stabilizing agent.

23 Claims, 3 Drawing Sheets

(56) References Cited

OTHER PUBLICATIONS

Cheng Yang "Stabilization of Copper/Zirconia Based Catalysts for Alcohol Synthesis" Prepr. Pap.-Am Chem, Soc., Div. Fuel Chem 48(2), 2003 p. 884-884.

C. Cannilla "Catalytic Behaviour of MnZrOx System for Heterogeneous Biodiesel Production" The Open Renewalbel Energy Journal 5, 2012 p. 32-40.

"Mn-stabilized zirconia catalyst for complete oxidation of n-butane", A. Keshavaraia, A. V. Ramaswamy, Applied Catalysis B: Environmental, 8, L1-L7, 1996.

"The thermal stability and catalytic application of MnOx-ZrO2 powder", thesis, by Qiang Zhao, Drexel University, 2004.

MANGANESE OXIDE-STABILIZED ZIRCONIA CATALYST SUPPORT MATERIALS

CROSS-REFERENCE TO RELATED APPLICATIONS

This application claims priority to U.S. Provisional Patent Application Ser. No. 61/840,038 filed Jun. 27, 2013, which is incorporated herein by reference in its entirety.

BACKGROUND OF THE INVENTION

1. Field of the Invention

The present disclosure relates generally to catalyst support materials, catalysts and methods for using them, such as methods for converting sugars, sugar alcohols, glycerol and organic acids to commercially-valuable chemicals and intermediates.

2. Technical Background

Zirconium oxide, also referred to as zirconia, has been used as a catalyst support material because of its high physical and chemical stability and moderate acidic surface properties. Nonetheless, the use of zirconia as a supporting material for heterogeneous catalysts has limited application due to its relatively high cost and difficulties in forming certain shapes from this material. Furthermore, the zirconia is especially susceptible to undergoing a phase transition that results in loss of surface area and pore volume. This reduces the strength and durability of the zirconia. To counteract these phase transformation effects, stabilizing agents are used to inhibit phase transformation from the preferable tetragonal phase to the less desirable monoclinic phase. Previously used stabilizing agents include, for example, silicon oxide, yttrium oxide, lanthanum oxide, tungsten oxide, magnesium oxide, calcium oxide, cerium oxide and chromium oxide.

Physical and chemical stability is a major concern in the application of heterogeneous catalysts in aqueous phase reactions. Traditional $SiO_2$ or $Al_2O_3$ based catalyst supports are prone to disintegration or attack when used in an aqueous solution, which usually results in loss of mechanical strength of the catalyst body that is targeted for a long-term industrial application. In laboratory and industrial applications, the mechanical strength of heterogeneous catalysts is generally evaluated by crush strength, wherein increasing crush strength values are generally indicative of improved mechanical strength of the support or carrier. Use of zirconia promoted with chromium oxide promoter materials yields a zirconia-based support or catalyst with improved physical properties for extrusion and/or use as a carrier or support for a catalyst in industrial applications performed in an aqueous environment. Chromium oxide-promoted zirconia support or catalyst shows no leaching into an aqueous solution, improving the mechanical strength and stability of the support/carrier or catalyst in various aqueous phase applications.

However, use of chromium-containing materials, especially chromium(VI) containing materials, is less desirable because of their toxic, corrosive, and carcinogenic properties. There remains a need environmentally nonhazardous materials that are also stable for hydrogenation/hydrogenolysis applications in aqueous phase.

SUMMARY OF THE INVENTION

In certain aspects, the present invention addresses the need for a chromium-free catalyst support suitable for aqueous phase applications. In various aspects, the disclosure provides a manganese-promoted zirconia support material that is hydrothermally stable, suitable for use in aqueous phase hydrogenolysis and hydrogenation, and can be easily extruded in the absence of any binder and/or extrusion aid. Manganese may serve as a textural promoter to stabilize zirconia in aqueous phase. Manganese may also serve as a chemical promoter to improve the catalytic performance, especially in hydrogenolysis.

Thus, in one aspect, the disclosure provides a catalyst support material including $ZrO_2$ and one or more oxides of manganese ($MnO_x$) the catalyst support material containing at least about 1 wt % of $MnO_x$. In certain embodiments, the weight percentage of $MnO_x$ in the catalyst support material is within the range of about 1 wt % to about 50 wt %; and/or the catalyst support material is substantially free of any binder, extrusion aid or additional stabilizing agent. In another embodiment, the catalyst support material is at least about 50 wt % $ZrO_2$ and $MnO_x$. In further embodiments, the weight ratio of $ZrO_2$ to $MnO_x$ is within the range of about 30:1 to about 1:1; and/or the catalyst support material is substantially free of any binder, extrusion aid or additional stabilizing agent.

In another aspect, the disclosure provides catalyst materials that include a catalyst support material as described herein, and a catalyst disposed on the catalyst support material. In certain embodiments, the catalyst can be a metallic catalyst, e.g., Ni, Cu, Co, Fe, Ru, Rh, Pd, Ag, Re, Os, Ir, Pt, Au, or any combination thereof, such as NiCu or NiSb.

In another aspect, the disclosure provides methods that utilize the catalyst support materials and catalyst materials as described herein. As will be described below, in certain embodiments the catalyst materials described herein are stable enough to be used in continuous aqueous phase reaction schemes, such as those in continuous stirrer tank reactors or fixed bed reactors. Accordingly, in one embodiment, a method for performing a catalytic reaction includes contacting one or more reactants with a catalyst material as described herein, wherein at least one of the reactants is in the aqueous phase. In certain embodiments, the reaction is conducted at a temperature within the range of 50° C. to 325° C. and a pressure within the range of about 10 bar to about 250 bar.

In particular, the disclosure provides methods for hydrogenation or hydrogenolysis of sugars, sugar alcohols and glycerol including contacting the sugar, sugar alcohol or glycerol with hydrogen and a catalyst material as described herein. For example, certain such methods include a process for converting a sugar, sugar alcohol or glycerol into a polyol or an alcohol comprising a shorter carbon-chain backbone by contacting the sugar, sugar alcohol or glycerol with hydrogen and a catalyst material as described herein.

The disclosure also provides methods to use the carrier or catalyst materials for hydrogenation of an organic acid, e.g., in an aqueous phase. For example, certain such methods include a process for reducing an organic acid (e.g., lactic acid, succinic acid, adipic acid, 3-hydroxypropionic acid, and/or a sugar acid) including contacting the organic acid with hydrogen and a catalyst material as described herein.

In another aspect, the disclosure also provides methods for preparing the catalyst support materials and catalyst materials as described herein. For example, in one embodiment, a catalyst support material is made by extruding a zirconia-manganese oxide precursor in the absence of any binder, extrusion aid or additional stabilizing agent. In one embodiment, a catalyst is made by extruding a catalytically active material-zirconia-manganese oxide precursor in the absence of any binder, extrusion aid, or additional stabilizing agent. In another embodiment, a catalyst is made by depositing one or more of catalytically active materials on to $ZrO_2/MnO_x$. Depositing may include, but is not limited to, impregnation, incipient wetness, precipitation, and physical mixing.

Specific embodiments of the present invention will become evident from the following detailed description of certain embodiments, examples, and the claims.

BRIEF DESCRIPTION OF THE SEVERAL VIEWS OF DRAWINGS

Figure 1:
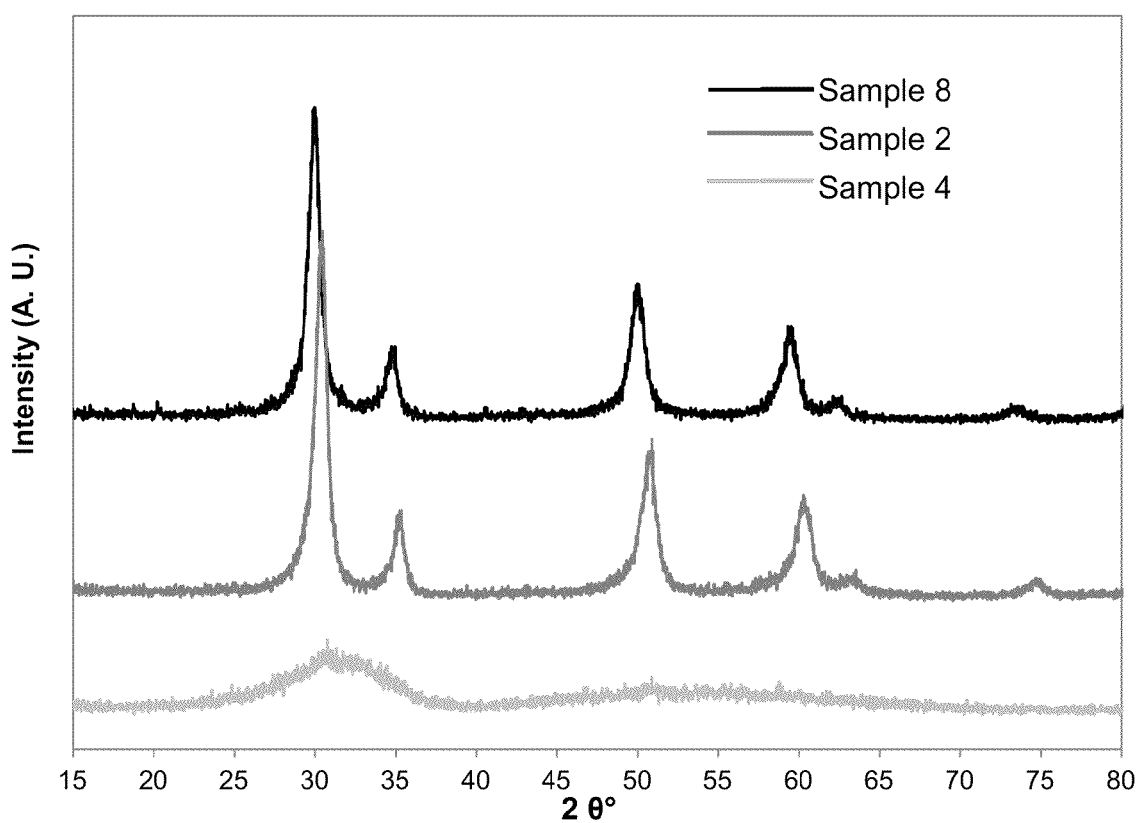
FIG. 1 shows the X-ray diffraction (XRD) patterns of $ZrO_2/MnO_x$ catalyst support material of Samples 2, 4, and 8.

In each Figure, the traces are provided in the same top-to-bottom order as in the legend.

DETAILED DESCRIPTION OF THE INVENTION

Before the disclosed methods and materials are described, it is to be understood that the aspects described herein are not limited to specific embodiments, apparati, or configurations, and as such can, of course, vary. It is also to be understood that the terminology used herein is for the purpose of describing particular aspects only and, unless specifically defined herein, is not intended to be limiting.

Throughout this specification, unless the context requires otherwise, the word "comprise" and "include" and variations (e.g., "comprises," "comprising," "includes," "including") will be understood to imply the inclusion of a stated component, feature, element, or step or group of components, features, elements or steps but not the exclusion of any other integer or step or group of integers or steps.

As used in the specification and the appended claims, the singular forms "a," "an" and "the" include plural referents unless the context clearly dictates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein the term "contacting" includes the physical contact of at least one substance to another substance.

All percentages, ratios and proportions herein are by weight, unless otherwise specified. A weight percent (weight %, also as wt %) of a component, unless specifically stated to the contrary, is based on the total weight of the formulation or composition in which the component is included (e.g., on the total amount of the active material), calculated as oxides for Mn, Zr, La, Y and other oxide constituents of the oxide materials of the catalyst support materials described herein.

In view of the present disclosure, the methods and active materials described herein can be configured by the person of ordinary skill in the art to meet the desired need. In general, the disclosed materials, methods, and apparati provide improvements in supports or carriers utilized in catalysis, particularly in aqueous phase hydrogenolysis and hydrogenation. For example, in certain aspect, the catalyst support materials are less environmentally hazardous than Cr-based materials, hydrothermally stable, suitable for use in continuous aqueous phase hydrogenolysis and hydrogenation, and can be easily extruded in the absence of any binder and/or extrusion aid.

One embodiment of the invention is a catalyst support material including comprising $ZrO_2$ and one or more oxides of manganese ($MnO_x$). As the person of ordinary skill in the art will appreciate, the oxidation state of manganese can be variable, and the manganese can be present in one or more of a variety of oxidation states within the material (e.g., Mn(0), Mn(II), Mn(III), Mn(IV)). The $MnO_x$ is present in the catalyst support material in an amount of at least about 1 wt %. In certain embodiments, $MnO_x$ in the catalyst support material is present in an amount within the range of about 1 wt % to about 50 wt %. In other embodiments, $MnO_x$ is present in an amount within the range from about 1 wt % to about 20 wt %, or about 1 wt % to about 15 wt %, or about 1 wt % to about 10 wt %, or about 1 wt % to about 8 wt %, or about 1 wt % to about 7 wt %, or about 3 wt % to about 15 wt %, or about 3 wt % to about 10 wt %, or about 3 wt % to about 7 wt %, or about 5 wt % to about 7 wt %, or about 5 wt % to about 8 wt %, or about 5 wt % to about 10 wt %.

The catalyst support material is at least about 50 wt % $MnO_x$ and $ZrO_2$, at least about 60 wt % $MnO_x$ and $ZrO_2$, at least about 70 wt % $MnO_x$ and $ZrO_2$, at least about 75 wt % $MnO_x$ and $ZrO_2$, at least about 80 wt % $MnO_x$ and $ZrO_2$, at least about 85 wt % $MnO_x$ and $ZrO_2$, at least about 90 wt % $MnO_x$ and $ZrO_2$, at least about 95 wt % $MnO_x$ and $ZrO_2$, or even at least about 99 wt % $MnO_x$ and $ZrO_2$.

The manganese oxide acts to stabilize the zirconia from undergoing the undesirable phase transition, for example, from the preferable tetragonal phase to the less desirable monoclinic phase. Accordingly, the ratio of $ZrO_2$ to $MnO_x$ can be important for the performance of the support material. Thus, in certain embodiments of the support materials and methods as described herein, the ratio (i.e., by weight, calculated as oxides) of $ZrO_2$ to $MnO_x$ is within the range of about 1:1 to about 30:1. In various embodiments of the catalyst support materials as described herein, the weight ratio of $ZrO_2$ to $MnO_x$ is within the range of about 1:1 to about 20:1, about 3:1 to about 30:1, about 5:1 to about 20:1, or about 11:1 to about 20:1, or about 12:1 to about 20:1, or about 13:1 to about 20:1, or about 14:1 to about 20:1, or about 15:1 to about 20:1, 12:1 to about 30:1, or about 15:1 to about 30:1, or about 20:1 to about 30:1, or about 25:1 to about 30:1. For example, in certain embodiments of the catalyst support materials as described herein, the weight ratio of $ZrO_2$ to $MnO_x$ is about 3:1, or about 5:1, or about 9:1, or about 13:1, or about 14:1, or about 15:1, or about 16:1, or about 17:1, or about 18:1, or about 19:1, or about 20:1, or about 25:1, or about 30:1. In one particular embodiment, the weight ratio of $ZrO_2$ to $MnO_x$ is in the range of about 1:1 to about 20:1. In certain embodiments, the weight ratio of $ZrO_2$ to $MnO_x$ is in the range of about 5:1 to about 25:1

Advantageously, the catalyst support materials described herein can be made without chromium, thus providing more environmentally benign materials. Accordingly, in one embodiment of the catalyst support materials as described herein, a catalyst support material is substantially free of chromium.

In certain embodiments of the catalyst support materials described herein, additional materials can be included. For example, in one embodiment of the catalyst support materials as described herein, a catalyst support material further includes oxides of yttrium and/or lanthanum, for example, in a weight ratio (i.e., calculated as oxides) within the range of about 10:1 to about 100:1 with respect to the $ZrO_2$. For example, in various embodiments of the catalyst support materials as described herein, the weight ratio of the oxides of Y and/or La to the $ZrO_2$ is within the range of about 50:1 to about 100:1, or about 20:1 to about 75:1, or about 15:1 to about 50:1. In particular embodiments, the weight ratio of the oxides of Y and/or La to the $ZrO_2$ is about 20:1, or about 30:1, or about 40:1, or about 50:1.

In certain embodiments, a catalyst support material as described herein includes (or, in one embodiment, consists essentially of) $ZrO_2$ in an amount within the range of about 50 to about 99 wt % (i.e., calculated as oxides); oxides of manganese in an amount within the range of about 1 to about 50 wt %; and optionally one or more oxides of yttrium and/or lanthanum in an amount up to about 10 wt %. For example, particular embodiments, a catalyst support material as described herein includes (or, in one embodiment, consists essentially of) $ZrO_2$ in an amount within the range of about 70 to about 99 wt %; oxides of manganese in an amount within the range of about 1 to about 30 wt %; and, optionally, one or more oxides of yttrium and/or lanthanum in an amount up to about 10 wt %.

As will be described in more detail below, the catalyst support material may be made via a number of different techniques familiar to the person of ordinary skill in the art. The catalyst support material can be made with a variety of crystalline forms, such as one or more of monoclinic, tetragonal, cubic and/or amorphous phases as determined by well-known powder x-ray diffraction (XRD) techniques and devices (e.g., see "Introduction to X-ray Powder Diffraction," R. Jenkins and R. L Snyder, Chemical Analysis, Vol. 138, John Wiley & Sons, New York, 1996). However, in certain advantageous embodiments, the $ZrO_2$ in the catalyst support material as described herein is mostly in a phase having tetragonal geometry, and has a relatively minor amount of $ZrO_2$ in the monoclinic phase. The inventors have determined that use of oxides of manganese, optionally in combination with oxides of yttrium and/or lanthanum, can stabilize the tetragonal phase of $ZrO_2$ relative to the less desirable monoclinic phase. Typically, the tetragonal phase of zirconium oxide may be determined by measuring the intensity of a sample at a d-spacing of 2.97 angstroms (A), while the monoclinic phase is measure at a d-spacing of 3.13 angstroms (A). For example, in certain embodiments, a catalyst support material as described herein has at least about 50 wt % of its $ZrO_2$ in the tetragonal phase. Similarly, in certain embodiments, a catalyst support material as described herein has less than 50 wt % of its $ZrO_2$ in the monoclinic phase. In other embodiments, a catalyst support material as described herein has at least about 80 wt % of its $ZrO_2$ in a tetragonal phase, and less than about 20 wt % of its $ZrO_2$ in a monoclinic phase. In one particular embodiment, a catalyst support material as described herein has within the range of about 85 wt to about 90 wt % of its $ZrO_2$ in a tetragonal phase and about 10 wt % to about 15 wt % of its $ZrO_2$ in a monoclinic phase.

Of course, the person of ordinary skill in the art will appreciate that the materials described herein can be provided in a variety of forms. For example, in other embodiments, the catalyst support material is provided in an amorphous form. As described below in more detail with reference to FIG. 3, crystalized zirconia (e.g., in a tetragonal phase) can be formed after hydrothermal treatment or after reaction in aqueous phase.

The catalyst support materials as described herein may be provided in any suitable form. For example, in various embodiments, a catalyst support material as described herein can be formed as spheres, pellets, cylinders (hollow or otherwise), symmetrical or asymmetrical tri-quadrulobes, for example, using extrusion methods as described below. The person of ordinary skill in the art will appreciate that the catalyst support materials can be provided in a variety of other forms.

The catalyst support materials described herein can be provided with a variety of different pore volumes, depending, e.g., on the methods used for making them and the desired end use. For example, in certain embodiments, a catalyst support material as described herein has a pore volume within the range of about 0.1 to about 1.5 $cm^3/g$, or about 0.2 to about 0.5 $cm^3/g$, or about 0.3 to about 0.5 $cm^3/g$, or about 0.4 to about 0.5 $cm^3/g$, or about 0.1 to about 1 $cm^3/g$. In various embodiments, a catalyst support material as described herein has a pore volume of about 0.1 $cm^3/g$, or about 0.2 $cm^3/g$, or about 0.3 $cm^3/g$, or about 0.4 $cm^3/g$, or about 0.5 $cm^3/g$, or about 1 $cm^3/g$, or about 1.5 $cm^3/g$. In particular embodiments, the catalyst support material has a pore volume within the range of about 0.2 to about 0.5 $cm^3/g$. In other particular embodiments, the catalyst support material has a pore volume within the range of about 0.3 to about 0.4 $cm^3/g$.

Similarly, the catalyst support materials described herein can be provided with a variety of different surface areas, depending, e.g., on the methods used for making them and the desired end use. For example, in certain embodiments, the surface area of a catalyst support material as described herein within the range of about 10 to about 400 $m^2/g$. The surface areas are measured using the Brunauer-Emmett-Teller (BET) Surface Area method. In certain embodiments, a catalyst support material as described herein has a surface area within the range of from about 10 to about 400 $m^2/g$, or about 50 to about 400 $m^2/g$, or about 70 to about 400 $m^2/g$, or about 100 to about 400 $m^2/g$, or about 200 to about 400 $m^2/g$, or about 300 to about 400 $m^2/g$, or about 10 to about 300 $m^2/g$, or about 50 to about 300 $m^2/g$, or about 70 to about 300 $m^2/g$, or about 100 to about 300 $m^2/g$, or about 200 to about 300 $m^2/g$, or about 10 to about 200 $m^2/g$, or about 50 to about 200 $m^2/g$, or about 70 to about 200 $m^2/g$, or about 100 to about 200 $m^2/g$. In one embodiment, a catalyst support material as described herein has a surface area of about 20 to about 300 $m^2/g$. In another embodiment, a catalyst support material as described herein has a surface area of about 30 to about 200 $m^2/g$. In another embodiment, a catalyst support material as described herein has a surface area of about 70 to about 300 $m^2/g$.

Likewise, the catalyst support materials described herein can be provided with a variety of different crush strengths, depending, e.g., on the methods used for making them and the desired end use. For example, in certain embodiments, a catalyst support material as described herein has a crush strength within the range of about 45 N/cm (i.e., ~1 lb/mm) to about 222 N/cm (i.e., ~5.0 lb/mm.) For example, in certain embodiments, a catalyst support material as described herein has a crush strength of at least 45 N/cm (i.e., ~1 lb/mm), or at least 67 N/cm (i.e., ~1.5 lb/mm), or at least 90 N/cm (i.e., ~2 lb/mm), or at least 134 N/cm (i.e., ~3 lb/mm), or at least 178 N/cm (i.e., ~4 lb/mm), depending on its use. In various embodiments, a catalyst support material as described herein has a crush strength within the range of about 45 N/cm to about 178 N/cm, or about 45 N/cm to about 134 N/cm, or about 45 N/cm to about 90 N/cm, or about 45 N/cm to about 67 N/cm, or about 67 N/cm to about 178 N/cm, or about 67 N/cm to about 134 N/cm, or about 67 N/cm to about 90 N/cm, about 90 N/cm to about 178 N/cm, or about 90 N/cm to about 134 N/cm. The crush strength of a catalyst or catalyst support/ carrier is measured using ASTM D6175-03 (2008), Standard Test Method for Radial Crush Strength of Extruded Catalyst and Catalyst Carrier Particles.

As will be described in further detail below, certain catalyst support materials as described herein can be prepared, for example, using extrusion methods without the use of any binder, extrusion aid or additional stabilizing agent. Accordingly, in certain embodiments, a catalyst support material as described herein is substantially free of any binder. In other embodiments, a catalyst support material as described herein is substantially free of any extrusion aid. For example, in one particular embodiment, a catalyst support material as described herein is substantially free of any binder and any extrusion aid. Moreover, as the manganese and the optional yttrium and/or lanthanum can stabilize the zirconia, in certain embodiments, a catalyst support material as described herein can be substantially free of an additional stabilizing agent. In certain embodiments, a catalyst support material as described herein is substantially free of any binder, extrusion aid or additional stabilizing agent. In all such embodiments, the catalyst support material can be provided as an extrudate.

The catalyst support materials described herein can be made using a variety of techniques. For example, in one embodiment a co-precipitation technique is used to make a catalyst support material as described herein. A zirconium compound and a manganese compound can be combined in aqueous solution and co-precipitated with base to co-precipitate a zirconia-manganese oxide precursor. Alternatively, the zirconium compound may be precipitated first and then the manganese compound may be mixed with the precipitated zirconia precursor to form the zirconia-manganese oxide precursor. The zirconia-manganese oxide precursor can then be dried, shaped and calcined in accordance with well-known processes to form a finished catalyst support material.

A variety of zirconium-containing compounds can be used as starting materials. For example, the zirconium compound may be selected from the group consisting of zirconium or zirconyl halides, zirconium or zirconyl nitrates, zirconium or zirconyl organic acids, and combinations thereof. Specific compounds include, for example, $ZrCl_4$, $ZrOCl_2$, $Zr(NO_3)_2 \cdot 5H_2O$, $ZrO(NO_3)_2$ and $ZrO(CH_3COO)_2$. Of course, as the person of ordinary skill in the art will appreciate, other zirconium compounds can be used; the processes described herein are not limited to the compounds specifically identified herein. In solution, zirconium can be in a form of zirconyl ($ZrO^{2+}$) or zirconium ion ($Zr^{4+}$ or $Zr^{2+}$) that may be obtained by dissolving corresponding salts in water.

Similarly, a wide variety of manganese-containing compounds can be used as starting materials. Manganese compounds can be, for example, in the form of halides, nitrates or organic acid salts similar to those described above with respect to the zirconium compound. One example of a manganese compound is $Mn(acac)_2$. In other embodiments (e.g., when the manganese compound is combined with the precipitated zirconia precursor), the manganese can be provided in the form of an oxide.

In a co-precipitation method for making the catalyst support materials as described herein, the zirconium compound and the manganese compound are dissolved, together with any other desired additives (e.g., yttrium and/or lanthanum compounds), in aqueous solution. In order to aid dissolution, the initial solution may be at an acidic pH, e.g., within the range of about 0.01 to about 4. Base, e.g., ammonia, ammonium hydroxide or sodium hydroxide, is then added to raise the pH of the solution, e.g., to within the range of about 8 to about 13, to precipitate the zirconia-manganese oxide precursor. Alternatively, a solution of base and a solution of metal precursor can be dropped into a matrix solution with controlled constant pH of 8 to about 13 during the entire precipitation. The person of ordinary skill in the art will select appropriate conditions depending on the starting materials, the desired end product, and the particular procedures used.

After the precipitation, the zirconia-manganese oxide precursor precipitate may be filtered or otherwise separated from the liquid. A variety of methods and/or apparatuses may be utilized, including the use of filter paper and vacuum pump, as well as centrifugal separation, other vacuum mechanisms and/or positive pressure arrangements. Optionally, the zirconia-manganese oxide precursor may be washed if any of the feed materials used in the process contain undesirable elements or compounds, such as chloride or sodium. Typically, one to ten washings, or even more washings may be desirable if undesired elements or other contaminants are present in the feed materials.

The zirconia-manganese oxide precursor can then be dried, using a variety of techniques and conditions as would be apparent to the person of ordinary skill in the art. The drying of the zirconia-manganese oxide precursor (e.g., when provided as a solid mass such as a filter cake) may be aided by dividing (e.g., breaking) it into smaller quantities. The division (e.g. breaking) of the filter-cake may be manual or automated. The zirconia-manganese oxide precursor may be dried at ambient conditions (e.g., room temperature and ambient pressure) or under moderate temperatures ranging up to about 120° C. In one embodiment, the zirconium-promoter precursor is dried at a temperature ranging between 40° C. and 90° C. for about 20 minutes to 20 hours, depending on the drying equipment used. In one embodiment, the zirconia-manganese oxide precursor is dried until a loss of ignition (LOI) is achieved in a range between about 65 wt % to about 75 wt %. As used herein, LOI may be understood as the weight loss percentage by ignition of the material at 480° C. for two hours. In other embodiments, the zirconia-manganese oxide precursor or the precipitated zirconium is dried until a LOI of about 69 wt % to 75 wt % is achieved. As will be appreciated by the person of ordinary skill in the art, the zirconia-manganese oxide precursor can be dried to a level that is desirable for a subsequent forming step. In many cases, it may be desirable to leave the zirconia-manganese oxide precursor a little wet to aid in forming.

In certain embodiments of the materials described herein, the zirconia-manganese oxide precursor may be dried to achieve a mixture that is suitable for extrusion without any binder(s), extrusion aid(s), or additional stabilizing agent(s). In other words, in certain embodiments of the catalyst support materials as described herein, the zirconia-manganese oxide precursor can be dried such that it can be extruded or otherwise formed into a shape suitable for a finished catalyst support material in the absence of any stabilizing agent, binder or extrusion aid. Accordingly, in certain embodiments, a catalyst support material or zirconia/manganese oxide precursor as described herein is substantially free of a binder, an extrusion aid, or an additional stabilizing agent. For example, in one embodiment, a catalyst support material or zirconia-manganese oxide precursor as described herein is substantially free of silicon oxide, tungsten oxide, magnesium oxide, calcium oxide, cerium oxide, other silicon compounds, silica-alumina compounds, graphite, mineral oil, talc, stearic acid, stearates and starch.

After being dried to a suitable level, the zirconia-manganese oxide precursor can be formed into any shape suitable for a catalyst support/carrier, using any of the forming methods familiar to the person of ordinary skill in the art. For example, in a particular embodiment of a method for making the catalyst support materials as described herein, the dried zirconia-manganese oxide precursor is formed by being extruded through a suitable die. Extrusion methods are well-known in the art. For example, a screw extruder, a press extruder, or any other extrusion devices and/or methods known in the art may be used. Alternatively, the zirconia-manganese oxide precursor may be formed by pressing, tabletting, pelleting, granulating, or even spray drying; the person of ordinary skill in the art will adjust the wetness of the zirconia-manganese oxide precursor to be suitable for the particular forming process used. Optionally, the extruded or otherwise formed zirconia-manganese oxide precursor may be further dried (for example, at moderate temperatures, e.g., up to about 120° C., for example, for a moderate period of time, e.g., typically about 1 to 5 hours) after being formed. Notably, in certain embodiments, a catalyst support material as described herein can be prepared by extruding a zirconia-manganese oxide precursor in the absence of any binder, extrusion aid or additional stabilizing agent.

To convert the extruded or otherwise formed zirconia-manganese oxide precursor into a catalyst support material, the zirconia-manganese oxide precursor can be calcined. For example, in certain embodiments of methods for making the catalyst support materials as described herein, the extruded or otherwise formed zirconia-manganese oxide precursor is calcined at a temperatures within the range of about 300° C. to about 1000° C., or in another embodiment, of about 400° C. to about 700° C. In various embodiments of methods for making the catalyst support materials as described herein, the extruded or otherwise formed zirconia-manganese oxide precursor is calcined at a temperature within the range of about 300° C. to about 1000° C., or of about 400° C. to about 700° C., or of about 500° C. to about 600° C., or of about 400° C. to about 500° C., or of about 400° C. to about 600° C., or of about 500° C. to about 700° C., or of about 600° C. to about 700° C. The calcination may last, for example, for a time within the range of about 2 to about 12 hours, or about 3 to about 5 hours, e.g., about 3 hours, about 4 hours, about 5 hours, or about 6 hours. In certain embodiments of methods for making the catalyst support materials as described herein, an extruded or otherwise formed zirconia-manganese oxide precursor is calcined at about 600° C. As is conventional in the art, a variety of heating programs can be used in calcining. For example, in certain embodiments, a slow temperature ramp may be used to avoid thermal shock of the material. In one particular embodiment, an extruded or otherwise formed zirconia-manganese oxide precursor as described herein may be calcined with heating at a rate of 3° C. per minute to 600° C. at which temperature the calcining continues for about 3 hours.

Certain particular methods for making catalyst support materials are described below in the Examples; the person of ordinary skill in the art can adapt these methods for making the catalyst support materials described generally herein.

The catalyst support materials as described herein may be combined with one or more catalytically active materials to form a catalyst for use in many industrial processes. Accordingly, another aspect of the invention is a catalyst material includes a catalyst support material as described herein, with a catalyst disposed thereon. The catalyst can be, for example, a metallic catalyst. In certain embodiments, a catalyst material includes a catalyst support material as described herein, and one or more metals selected from the group VIII. In certain embodiments, the catalytic metal can be Ni, Cu, Co, Fe, Ru, Rh, Pd, Ag, Re, Os, Ir, Pt, Au, or any combination thereof. In some embodiments, the catalytic material is Ni, Cu, NiCu, NiCuBi or NiSb. Of course, the person of ordinary skill in the art will appreciate that the catalyst support materials can be useful with other catalysts, for example, palladium, platinum, rhodium and ruthenium.

The person of ordinary skill in the art will determine the appropriate level of catalyst loading on the catalyst support. In certain embodiments, a catalyst material includes (or consists essentially of) in the range of about 50 to about 95 wt % of a catalyst support material as described herein, and about 5 to about 50 wt % of a catalyst (e.g., a metallic catalyst) as described herein. For example, in one embodiment, a catalyst material includes (or consists essentially of) in the range of about 60 to about 95 wt % of a catalyst support material as described herein, and about 5 to about 40 wt % of a catalyst (e.g., a metallic catalyst) as described herein. In another embodiment, a catalyst material includes (or consists essentially of) in the range of about 70 to about 95 wt % of a catalyst support material as described herein, and about 5 to about 30 wt % of a catalyst (e.g., a metallic catalyst) as described herein.

The catalyst support materials and catalyst materials described herein can, in certain embodiments, exhibit high hydrothermal and mechanical stability, and thus can be suitably durable for advantageous use in aqueous phase hydrogenation or hydrogenolysis reactions, such as the conversion of sugars, sugar alcohols or glycerol. Accordingly, additional aspects of the invention relate to various uses of the catalyst support materials and catalyst materials described herein. For example, one embodiment of the invention is a method of conducting a catalytic reaction including contacting one or more reactants with a catalyst material as described herein, wherein at least one of the reactants is in the aqueous phase. Such reactions can, in certain embodiments, be conducted at relatively high temperatures (e.g., in the range of 50° C. to 325° C., or in the range of about 90° C. to about 275° C.), and/or at relatively high pressures (e.g., in the range of about 10 bar to about 250 bar, or in the range of about 50 bar to about 200 bar). In certain embodiments, at least one reactant is a gas (e.g., hydrogen), provided at partial pressure that is at least about 20%, at least about 50%, or even at least about 90% of the overall pressure.

The catalyst support materials and catalyst materials described herein can be especially useful in catalytic hydrogenation or hydrogenolysis of a sugar, a sugar alcohol, or glycerol, for example, into commercially-valuable chemical products and intermediates, including, but not limited to, polyols or an alcohol comprising a shorter carbon-chain backbone such as propylene glycol (1,2-propanediol), ethylene glycol (1,2-ethanediol), glycerin, trimethylene glycol (1,3-propanediol), methanol, ethanol, propanol and butandiols. As used herein, unless otherwise qualified, the term polyol(s) refers to any polyhydric alcohol containing more than one hydroxyl group. As broadly defined, the term polyol may encompass both the reactants and/or the products described above. Thus, one embodiment of a catalytic method as described herein includes contacting a sugar, a sugar alcohol or glycerol and hydrogen with a catalyst material as described herein (e.g., with Ni, Cu, Co, Fe, Ru, Rh, Pd, Ag, Re, Os, Ir, Pt, Au, or any combination thereof as the catalytic metal). The contacting can be performed at a relatively high temperature and/or pressure as described above. The methods described herein can be performed to achieve, for example, at least 40% efficiency, and a total carbon atom selectivity of at least 70 mol %.

As described below with respect to Example 4, catalyst materials including manganese can perform better than similar catalyst materials including chromium. Without intending to be bound by theory, the inventors believe that the manganese acts as a promoter for the catalyst, e.g., for a nickel-containing catalyst. Accordingly, in certain embodiments, a catalyst material includes manganese (e.g., in oxide form or in metallic form) in the presence of one or more additional catalytic metals. For example, in certain embodiments, a catalyst material includes manganese in combination with nickel (e.g., in the form of NiSb or NiCu).

The catalyst support materials and catalyst materials described herein can also be useful in catalytic hydrogenation of organic acids into commercially-valuable chemical products and intermediates. Exemplary organic acids include, but are not limited to, acetic acid, formic acid, propionic acid, butyric acid, caproic acid, glycolic acid, lactic acid, 3-hydroxypropionic acid, hydroxylbutyric acid, hydroxycyclopentanoic acid, salicylic acid, mandelic acid, benzoic acid, fatty acids, and sugar acids. A used herein, unless otherwise noted, the term sugar acid(s) refers to any monosaccharide containing one or more carboxylic acid moieties. Examples include, but are not limited to glyceric acid, xylonic acid, gluconic acid, ascorbic acid, tartaric acid, mucic acid, saccharic acid, glucuronic acid, and galacturonic acid. The organic acids may also include polycarboxylic acid compounds, such as tartaric acid, citric acid, malic acid, oxalic acid, succinic acid, adipic acid, malonic acid, galactaric acid, 1,2-cyclopentane dicarboxylic acid, maleic acid, fumaric acid, itaconic acid, phthalic acid, terephthalic acid, phenylmalonic acid, hydroxyphthalic acid, dihydroxyfumaric acid, tricarballylic acid, benzene-1,3,5-tricarboxylic acid, isocitric acid, mucic acid and glucaric acid. In one embodiment of the disclosure, the organic acid is selected from lactic acid, succinic acid, adipic acid, and various sugar acids. Thus, one embodiment of a catalytic method as described herein includes contacting an organic acid and hydrogen with a catalyst material as described herein (e.g., with Ni, Cu, Co, Fe, Ru, Rh, Pd, Ag, Re, Os, Ir, Pt, Au, or any combination thereof as the catalytic metal). The contacting can be performed at a relatively high temperature and/or pressure as described above. The methods described herein can be performed to achieve, for example, at least 40% efficiency, and a total carbon atom selectivity of at least 70 mol %.

The catalyst materials described herein can be made by any suitable method. For example, a catalyst (e.g., a metallic catalyst) can be disposed on a catalyst support material as described herein using conventional methods, for example, by depositing the catalyst thereon. Depositing may include, but is not limited to, impregnation, incipient wetness, precipitation, and physical mixing. Alternatively, the catalyst can be provided at any stage in the formation of the catalyst support material (e.g., as the catalyst itself or as some precursor for the catalyst that gets converted to catalytically active material in a later step). For example, in some embodiments, a catalyst is made by extruding a catalyst-$ZrO_2/MnO_x$ precursor in the absence of any binder, extrusion aid, or additional stabilizing agent.

EXAMPLES

The following examples are presented to illustrate the embodiments of the present invention and are not intended to constitute a limitation on their scope, which is defined in the appended claims.

Example 1

Catalyst support materials were prepared by co-precipitation of manganese(II) acetate ($Mn(OAc)_2$) and zirconyl nitrate ($ZrO(NO_3)_2$) precursors, using NaOH for precipitation. In a typical preparation, 80 g of $Mn(OAc)_2$ was dissolved into 924 g of zirconyl nitrate solution (20 wt % $ZrO_2$) and precipitated with 25 wt % NaOH solution. The precipitation was conducted at a pH in the range of about 8.5 to about 10.5. The precipitate was aged overnight and washed with excess de-ionized water until the conductivity of the final, filtered water was less than 0.4 mS/cm. Then, the filtration cake was dried to a loss of ignition (LOI) in the range of 68-74% and extruded using an extruder. The extrudates so-formed were dried at 110° C. for 3 h, followed by calcination at temperatures ranging from 450° C. to 675° C. for 3 h with heating ramp rate of 3K/min.

Table 1 lists seven of the preparations and their physical properties. Mn content on $ZrO_2/MnO_x$ catalyst support materials varied from 5 wt % to 27 wt % by X-ray fluorescence (XRF) bulk analysis. The extrudates showed good crush strength of approximate 2 lbs/mm to 3 lbs/mm and good pore volume of 0.35 mL/g up to 0.59 mL/g. The Brunauer-Emmett-Teller surface area (BET S.A.) varied from 85 $m^2$/g to 200 $m^2$/g, depending on Mn content and on calcination temperatures. The extrudates also showed good attrition resistance with less than 4% attrition.

TABLE 1

The properties of catalyst support materials prepared by co-precipitation

| Sample No. | Mn wt % | Crush strength (lb/mm) | Pore volume (mL/g) | BET S.A. ($m^2$/g) | Attrition (%) | Calcination Temp. (° C.) |
| --- | --- | --- | --- | --- | --- | --- |
| 1 | 5 | 2.9 | 0.34 | 85 | 1.2 | 600 |
| 2 | 7 | 1.8 | 0.43 | 102 | 3.3 | 600 |
| 3 | 7 | 2.0 | 0.55 | 185 | 2.1 | 450 |
| 4 | 10 | 2.12 | 0.59 | 177 | 3.5 | 550 |
| 5 | 27 | 2.7 | 0.55 | 171 | 3.1 | 550 |
| 6 | 15 | 1.8 | 0.53 | 201 | 2.0 | 550 |
| 7 | 22 | 2.9 | 0.46 | 207 | 2.8 | 550 |

Example 2

Ternary catalyst support materials or catalysts were prepared by co-precipitation methods. Table 2 listed five of the preparations. Samples 8 and 9 were yttrium and lanthanum stabilized $ZrO_2/MnO_x$ materials, in which the yttrium and lanthanum were present as oxides. In a typical preparation, 60.8 g of $Mn(oAc)_2$ and 26.1 g of $Y(NO_3)_3.6H_2O$ was dissolved into 702 g of $ZrO(NO_3)$ solution (20 wt % $ZrO_2$) and precipitated with 25 wt % NaOH solution. The precipitation was conducted at a pH in the range of about 8.5. The precipitate was aged overnight and washed with excess de-ionized water until the conductivity of the final, filtered water was less than 0.2 mS/cm. Then, the filtration cake was dried to a loss of ignition (LOI) in the range of 68-74% and then extruded. The extrudates were then dried at 110° C. for 3 h and calcination at 550-675° C. for 3 h with a heating ramp rate of 3 K/min. Samples 9-12 were prepared using procedures similar to that described above, using $La(NO_3)_3.6H_2O$, $Cu(NO_3)_2.2.5H_2O$, $Ni(NO_3)_2$ solution (13.8 wt. %) as precursors.

Table 2 lists the basic physical properties of these materials. All the materials showed good crush strength of 2 lbs/mm to 3 lbs/mm and good attrition resistance of less than 3.5% attrition. The pore volume varied from 0.2 to 0.35 mL/g. Except for sample 12, all the materials yielded good surface area about 160 $m^2$/g. The calcination temperature was important for surface area. Notably, Samples 10-12 include coextruded catalyst (Ni, NiCu and Cu, respectively), present in the finished catalyst material in metallic form. Samples 10-12 were used as catalyst for hydrogenation/hydrogenolysis.

TABLE 2

The properties of ternary catalyst support materials or catalyst materials prepared by co-precipitation.

| Sample No. | composition wt. % (oxide basis) | Crush strength (lb/mm) | Pore volume (mL/g) | BET S.A ($m^2$/g) | Attrition (%) | Calcination Temp. (° C.) |
|---|---|---|---|---|---|---|
| 8 | Mn 7%; Y 3.5% | 2.06 | 0.28 | 163 | 2.8 | 550 |
| 9 | Mn 6%; La 12% | 3.18 | 0.19 | 166 | 2.4 | 550 |
| 10 | Mn 5%; Ni 10% | 2.45 | 0.35 | 181 | 3.0 | 550 |
| 11 | Mn 5%; Ni 10%; Cu 1% | 2.10 | 0.33 | 161 | 3.5 | 550 |
| 12 | Mn 9%; Cu 10% | 2.27 | — | 30 | 2.2 | 600 |

Results

Samples 4, 2 and 8 were evaluated by XRD, and the results are shown in FIG. 1. Sample 4 (about 10 wt. % Mn content) was prepared by calcination at 550° C. for 3 h, and proved to be XRD amorphous. Sample 2 (about 7 wt. % Mn content) was prepared by calcination at 600° C., and a stabilized tetragonal zirconia phase was observed by XRD. The phase transition temperature from amorphous material to stabilized zirconia increased with increasing Mn content. For example, in this particular example, a minimal 650° C. was required to obtain a stabilized tetragonal zirconia-manganese with about 26 wt. % Mn.

Sample 8 (about 7 wt. % Mn and 3.5 wt. % Y content) was prepared by calcination at 550° C. for 3 h. With addition of Y, the phase transition temperature decreased. Y, in addition to Mn, stabilized zirconia in tetragonal phase.

Hydrothermal stability tests over Sample 2 and Sample 5 were conducted at 230° C. under 80 bar nitrogen for 3 days or 6 days in aqueous diluted NaOH solution (pH of 12). No leaching of metals in aqueous solution was observed for any of the above materials.

Hydrothermal stability (HT) tests over Sample 2 and Sample 5 were also conducted at 230° C. under 80 bar hydrogen for 3 days or 6 days in diluted aqueous NaOH solution (pH of 12). Before the HT tests, the carrier was reduced in-situ at 450° C. for 4 h with a heating ramp rate of 5 K/min. No leaching of these reduced materials was observed in aqueous solution.

Figure 2:
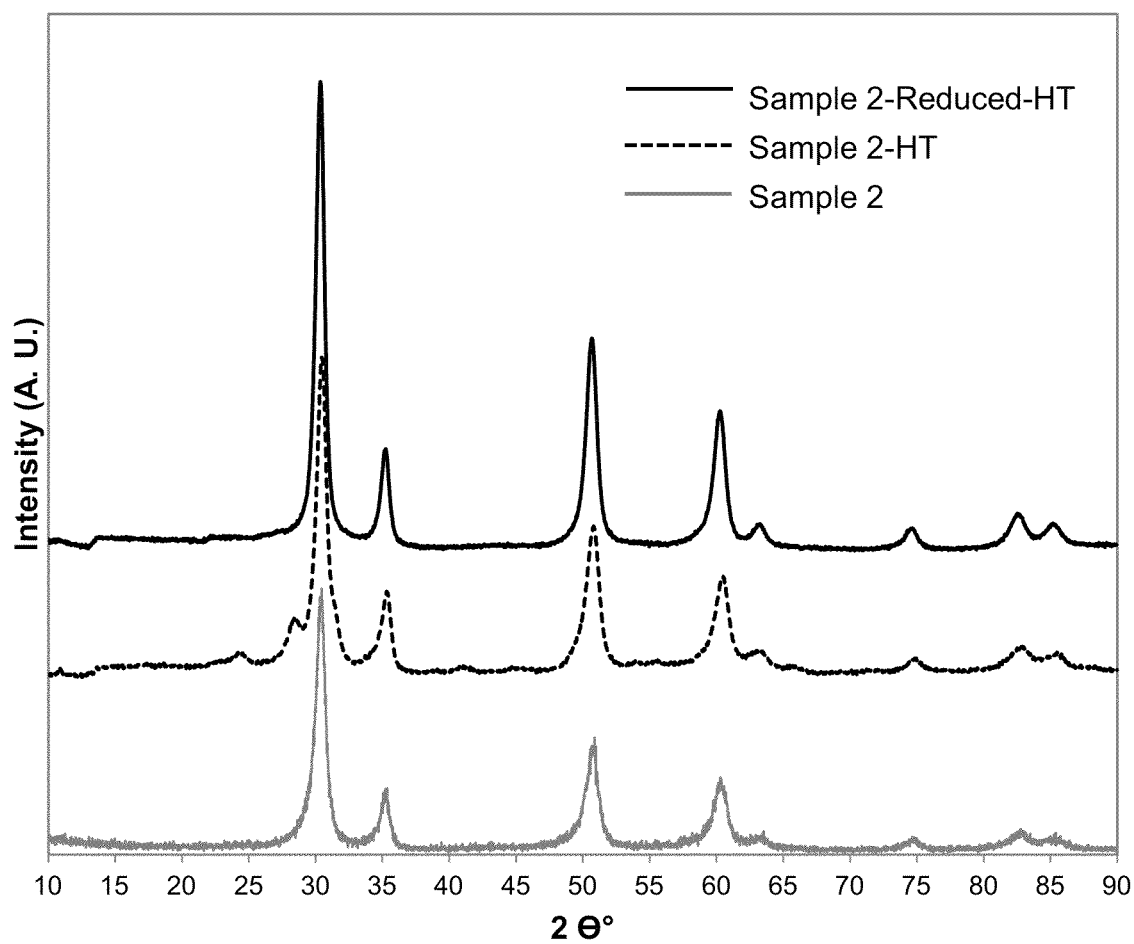
FIG. 2 shows the XRD patterns of $ZrO_2/MnO_x$ catalyst support material Sample 2, Sample 2 after the hydrothermal treatment, and Sample 2 after reduction and hydrothermal treatment.

XRD patterns of Sample 2, Sample 2 after HT treatment and Sample 2 after reduction and HT treatment are shown in FIG. 2. Both HT sample 2 and reduced HT sample 2 maintained the stabilized tetragonal crystal structure. A minor phase segregation was observed in the HT sample but not in the reduced and HT sample.

Figure 3:
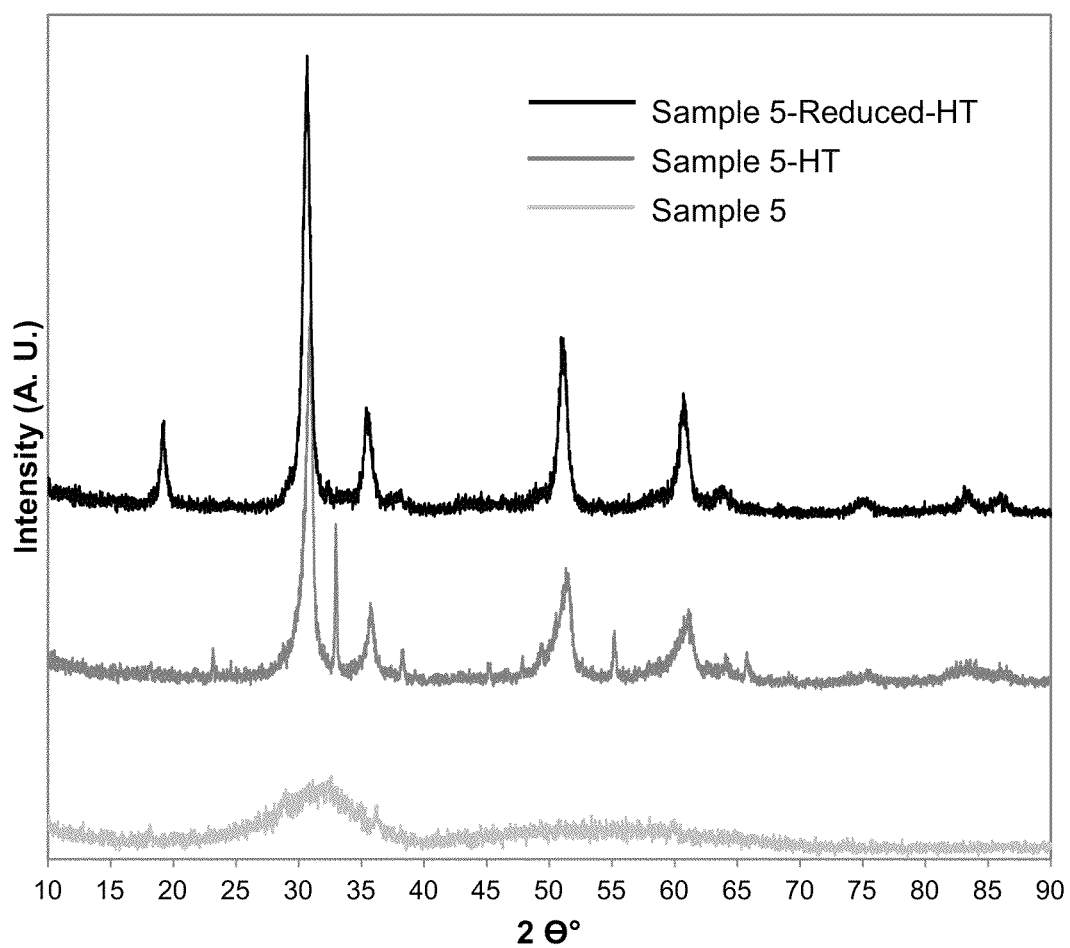
FIG. 3 shows the XRD patterns of $ZrO_2/MnO_x$ catalyst support material Sample 5, Sample 5 after the hydrothermal treatment, and Sample 5 after reduction and hydrothermal treatment.

XRD patterns of Sample 5, Sample 5 after HT treatment and Sample 5 after reduction and hydrothermal treatment are shown in FIG. 3. Sample 5 is XRD amorphous; however, after hydrothermal treatment, the material was crystalized with stabilized tetragonal phase, and $MnO_x$ (α-$Mn_2O_3$ and $Mn_3O_4$). Sample 5 after reduction and HT treatment, a Mn stabilized tetragonal phase and MnO phase was seen.

Example 3

Eight catalyst materials were prepared by impregnation (Imp) method or incipient wetness (IW) method on $ZrO_2$/$MnO_x$ support materials, and are listed in Table 3. $ZrO_2$/$CrO_x$ was prepared with Ni (10 wt. %) and Cu (1 wt. %) by incipient wetness method (Sample 13) for comparison purpose. To prepare Ni—, NiCu— and Cu-containing catalysts, nickel nitrate and copper nitrate were used as precursors. To prepare NiSb-containing catalyst, antimony nitrate was first dissolved in citric acid and then mixed with nickel nitrate solution as precursor solution. Sample 18 (Ru—$ZrO_2$/$MnO_x$) was prepared by incipient wetness method. Hexaammine-ruthenium (III) chloride (Ru($NH_3$)$_6$$Cl_3$) was used as catalyst precursor. The catalyst was dried at 45° C. for a couple of hours and then reduced in-situ with a hydrogen gas hour space velocity (GHSV) of 1000/h.

All the catalyst materials required a reduction step. Generally, Ni and NiCu catalyst materials were reduced at 450° C. for 4 hours with a flow of ambient pressure of hydrogen (GHSV of 1000/h) and heating ramp rate of 5 K/min. The Cu catalyst material (Sample 21) was reduced at 250° C. for 2 hours with a heating ramp rate of 0.5 K/min with hydrogen flow. The Ru catalyst material (Sample 18) was reduced at 230° C. for 3 hours with a heating ramp rate of 2.5 K/min in a hydrogen flow.

TABLE 3

Catalyst materials prepared on $ZrO_2$/$MnO_X$ support materials.

| Sample No. | Catalyst type | composition wt % (oxide basis) | Preparation method |
|---|---|---|---|
| 13 | NiCu—$ZrO_2$/$CrO_X$ | Ni 10%; Cu 1% | IW |
| 14 | NiCu—$ZrO_2$/$MnO_X$ | Ni 10%; Cu 1%; Mn 6% | IW |
| 15 | NiCu—$ZrO_2$/$MnO_X$ | Ni 17%; Cu 5%; Mn 5% | Imp |
| 16 | NiCu—$ZrO_2$/$MnO_X$ | Ni 17%; Cu 5%; Mn 21% | Imp |
| 17 | NiSb—$ZrO_2$/$MnO_X$ | Ni 10%; Sb 0.3%; Mn 6% | IW |
| 18 | Ru—$ZrO_2$/$MnO_X$ | Ru 1%; Mn 27% | IW |
| 19 | Ni—$ZrO_2$/$MnO_X$ | Ni 20%; Mn 22% | IW |
| 20 | Ni—$ZrO_2$/$MnO_X$ | Ni 20%; Mn 6% | Imp |
| 21 | Cu—$ZrO_2$/$MnO_X$ | Cu 10%; Mn 24% | Imp |

Example 4

A NiCu—$ZrO_2$/$MnO_x$ catalyst material (Sample 14) was studied for xylitol hydrogenolysis and was compared to NiCu prepared on $ZrO_2$/$CrO_x$ (Comparative Sample 13). The test was conducted in a batch reactor under 100 bar of hydrogen pressure at 210° C. for 6 h. Before the test, the catalysts were reduced at 450° C. for 4 h with a heating ramp rate of 5 K/min. The feed in each test contained about 25 wt % xylitol with co-feed of NaOH (xylitol/NaOH molar ratio=10). The catalysts were sized to about Ø1.8×1.8 mm and loaded into a basket in reactor. The total catalyst loading was 5 mL, and the total liquid feed was 100 mL.

Xylitol hydrogenolysis produces ethylene glycol (EG), propylene glycol (PG) and glycerin (GLY) as major reaction products. Side products includes lactic acid, arobitol, threitol, butandiols and reaction intermediates glycolaldehyde and glyceraldehyde. The conversion efficiency and selectivities based on the carbon content are calculated as follows:

$$\text{Conversion} = \frac{\text{mol. of xylitol } consumd}{\text{mol. of xylitol input}} \times 100\%$$

$$S_{EG} = \frac{\text{mol. of } EG \times 2}{\text{mol. of xylitol consumed} \times 5} \times 100\%$$

$$S_{PG} = \frac{\text{mol. of } PG \times 3}{\text{mol. of xylitol consumed} \times 5} \times 100\%$$

$$S_{GLY} = \frac{\text{mol. of } GLY \times 3}{\text{mol. of xylitol consumed} \times 5} \times 100\%$$

Total carbon selectivity = $S_{EG} + S_{PG} + S_{GYL}$

The catalytic performance after 6 h reaction is noted in Table 4. The same NiCu—ZrO$_2$/MnO$_x$ (Sample 14) showed much improved activity and selectivity compared to NiCu—ZrO$_2$/CrO$_x$ (Sample 13). The conversion was 98.8% after 6 h reaction over NiCu—ZrO$_2$/MnO$_x$ compared to 80.8% conversion over NiCu—ZrO$_2$/CrO$_x$ catalyst under the same reaction conditions. The NiCu catalyst on ZrO$_2$/MnO$_x$ also showed about 20% higher PG selectivity and 4% higher EG selectivity at 42% PG and 22% EG, respectively. Without intending to be limited by theory, the inventors believe that the manganese acts as a promoter for the nickel-based catalyst.

h with a heating ramp rate of 5 K/min. The feed in each test contained about 25 wt % xylitol with co-feed of NaOH (xylitol/NaOH molar ratio=10). The hydrogen flow was maintained at hydrogen/xylitol mol. ratio of 10.

The test lasted for more than 260 h with variable testing conditions in order to achieve optimized conversion and selectivity. The conversion efficiency and the carbon selectivity were calculated as shown above, and the results are summarized in Table 5. Sample 15 showed the highest selectivity with 27.2% EG selectivity and 45.6% PG selectivity with about 96.8% xylitol conversion at 230° C. with LHSV of 3/h. Sample 16 showed similar performance but at lower reaction temperature of 210° C. compared to 230° C. over sample 15, but about 2.6% lower of conversion and 2.2% lower of total carbon selectivity. Sample 11 showed 97% conversion under 120 bar of hydrogen at 210° C. with LHSV of 2/h. The carbon total carbon selectivity was low at only 69.2%: 24% EG, 39% PG, and 6% GLY selectivity. NiSb-containing Sample 17 showed the lowest activity and selectivity under similar conditions.

TABLE 5

Catalytic performance of ZrO$_2$/MnO$_X$ based catalyst materials for xylitol hydrogenolysis.

| | Sample No. | | | |
|---|---|---|---|---|
| | 15 | 16 | 11 | 17 |
| | Cat. type | | | |
| Catalyst | NiCu—ZrO$_2$/MnO$_X$ | NiCu—ZrO$_2$/MnO$_X$ | NiCu—ZrO$_2$/MnO$_X$ | NiSb—ZrO$_2$/MnO$_X$ |
| Operating Conditions | 120 Bar H$_2$ LHSV: 3 h$^{-1}$ 230° C. | 120 Bar H$_2$ LHSV: 3 h$^{-1}$ 210° C. | 120 Bar H$_2$ LHSV: 2 h$^{-1}$ 210° C. | 120 Bar H$_2$ LHSV: 1 h$^{-1}$ 210° C. |
| Total hours on stream | 362 | 352 | 352 | 260 |
| Xylitol conversion % | 96.8 | 94.2 | 97.1 | 93.9 |
| CS* to EG % | 27.2 | 26.2 | 24.0 | 21.1 |
| CS to PG % | 45.6 | 41.9 | 39.1 | 40.0 |
| CS to Gly % | 3.0 | 6.0 | 6.1 | 3.2 |
| Total CS % | 76.3 | 74.1 | 69.2 | 64.30 |

*carbon selectivity

TABLE 4

Catalytic performance of NiCu—ZrO$_2$/CrO$_X$ and NiCu—ZrO$_2$/MnO$_X$ materials for xylitol hydrogenolysis.

| Sample | | | $S_C$* % | | |
|---|---|---|---|---|---|
| No. | Catalyst type | Conversion % | EG | PG | Total |
| 13 | NiCu—ZrO$_2$/CrO$_X$ | 80.8 | 18 | 22 | 55 |
| 14 | NiCu—ZrO$_2$/MnO$_X$ | 98.8 | 22 | 42 | 69.1 |

*carbon selectivity

Example 5

Several samples were studied for xylitol hydrogenolysis in a trickle bed reactor: Sample 11, Sample 15, Sample 16, and Sample 17. The test was conducted under 80-120 bar of hydrogen pressure with variation of reaction temperature and liquid hour space velocity (LHSV). The catalyst loading was about 15 to 30 mL and diluted in SiC by 1 to 1 volumetric ratio. Before test, the catalysts were reduced at 450° C. for 4

Example 6

Samples 10, 11, 14, 19 and 20 were evaluated for xylose hydrogenation in a batch reactor. Before reaction, the catalysts were reduced in-situ at 450° C. for 4 h with a heating ramp rate of 3 K/min. The test was conducted under 80 bar hydrogen pressure at 120° C. for 6 h. The catalyst loading was about 5 mL (about 5.1-5.5 g) in each test. The feed contained about 10 wt % xylose (food grade) aqueous solution with total about 100 mL in volume. The conversion efficiency and selectivity for xylitol was determined as follows:

$$\text{Conversion} = \frac{\text{mol. of xylose consumd}}{\text{mol. of xylose input}} \times 100\%$$

$$S_{xylitol} = \frac{\text{mol. of xylitol produced} \times 5}{\text{mol. of xylose consumed} \times 5} \times 100\%$$

The conversion and xylitol selectivity from xylose hydrogenation after 6 h is shown in Table 6. For all the catalyst materials, the conversion was high (above 98%), but the xylitol selectivity varied. NiCu catalyst material showed a higher selectivity compared to Ni catalyst material; for example, NiCu—ZrO$_2$/MnO$_x$ (Sample 14) showed about 99.9% xylitol selectivity while Ni—ZrO$_2$/MnO$_x$ (Sample 20) showed about 90.9% xylitol selectivity, where the catalysts were prepared based on the same carrier. The carbon selectivity to xylitol dropped significantly from 90.9% for Sample 20 to only 50% for Sample 19, both of which are Ni—ZrO$_2$/MnO$_x$ materials but the later had a much higher Mn loading. For Sample 19, about 12% GYL selectivity, about 10% EG selectivity, and about 10% PG selectivity were observed in the final product, and the other carbon was possibly lost as coke and in gas.

TABLE 6

Catalytic performance of ZrO$_2$/MnO$_X$ based catalyst materials for xylose hydrogenation.

| Sample | | Xylose Hydrogenation (6 h) | |
|---|---|---|---|
| No. | Catalyst ID. | Conversion (%) | Xylitol selectivity (%) |
| 20 | Ni—ZrO$_2$/MnO$_X$ | 99.6 | 90.9 |
| 14 | NiCu—ZrO$_2$/MnO$_X$ | 99.1 | 99.9 |
| 19 | Ni—ZrO$_2$/MnO$_X$ | 98.6 | 50.6 |
| 10 | Ni—ZrO$_2$/MnO$_X$ | 100 | 94.4 |
| 11 | NiCu—ZrO$_2$/MnO$_X$ | 99.6 | 100 |

Example 7

Lactic acid (LA) is able to be produced by sugar fermentation. It is also the by-product of sugar alcohol hydrogenolysis with about 5 to 10% carbon selectivity. Lactic acid hydrogenation produces 1,2-propylene glycol (1,2-PG).

Sample 18, Ru—ZrO$_2$/MnO$_x$, was evaluated for LA hydrogenation in a continuous stirred tank reactor (CSTR). The feed contained about 4.5 wt % LA; the catalyst loading was 5 mL and the reactor volume was 150 mL. The catalyst was reduced in-situ at 230° C. for 3 h with a heating ramp rate of 2.5 K/min. The reaction started at 110° C. with liquid residence time of 3 h under 80 bar of hydrogen with a flow of 80 mL/min. After 21 hours, no obvious conversion of LA was seen. The reaction temperature was then increased to 150° C. and liquid residence time was increased to 4.5 hours. The reaction lasted for about 42 hours under this condition. Two samples were collected at 22 and 42 hours, and the conversion efficiency and 1,2-propylene glycol yield were determined as below:

$$\text{Conversion} = \frac{C_{LA}^0(\text{mol.}) - C_{LA}(\text{mol.})}{C_{LA}^0(\text{mol.})} \times 100\%$$

$$\text{Yield} = \frac{C_{1,2PG}(\text{mol.})}{C_{LA}^0(\text{mol.})} \times 100\%$$

The catalyst showed about 23-24% conversion with about 23% 1,2-PG yield (on carbon basis) (Table 7). There was no other product observed by HPLC analysis. The activity and selectivity were stable during 42 h test.

TABLE 7

Catalytic performance of Ru—ZrO$_2$/MnO$_X$ (Sample 18) material for lactic acid hydrogenation in a CSTR with residence time of 4.5 h at 150° C. under 80 bar of hydrogen pressure.

| | LA Hydrogenation | |
|---|---|---|
| Reaction time (h) | Conversion (%) | 1,2 PG Yield (%) |
| 22 | 24.7 | 23.8 |
| 42 | 23.4 | 23.3 |

Example 8

Sample 21 (Cu—ZrO$_2$/MnO$_x$) and Sample 12 (Cu—ZrO$_2$/MnO$_x$) were evaluated for glycerin hydrogenolysis in a batch reactor with and without addition of NaOH to adjust feed pH. Before reaction, the catalysts were reduced in-situ at 250° C. for 2 h with a very slow heating ramp rate of 0.5 K/min. The GHSV of hydrogen for reaction was maintained at 2000/h in order to remove the heat generated by reduction immediately. The test was conducted under 100 bar of hydrogen pressure at 220° C. for 6 h. The catalyst loading was about 5 mL (about 5.5 g) in each test; and the feed contained about 40 wt % glycerin aqueous solution with total volume of 100 mL. The conversion efficiency and 1,2-PG selectivity were calculated as follows:

$$\text{Conversion} = \frac{\text{mol. of } GLY \text{ consumd}}{\text{mol. of } GLY \text{ input}} \times 100\%$$

$$S_{1,2PG} = \frac{\text{mol. of } 1,2 \ PG \text{ produced} \times 3}{\text{mol. of } GLY \text{ consumed} \times 3} \times 100$$

The reaction was performed for 6 hours, and the results are shown in Table 8. Sample 12, which was prepared by co-precipitation method, showed about 63% conversion with 90.3% 1,2-PG selectivity with starting glycerin solution at a pH of 12.5. Sample 21 (prepared by impregnation with high Mn content) showed slightly lower 1,2-PG selectivity at starting pH of 12. However, the conversion of glycerin increased by about 11.6% after 6 hours when the starting pH of glycerin solution was 12.

TABLE 8

Catalytic performance of Cu—ZrO$_2$/MnO$_X$ materials for glycerin hydrogenolysis.

| | | | Glycerin Hydrogenolysis (6 h) | |
|---|---|---|---|---|
| Sample No. | Catalyst type | Start pH | Conversion (%) | 1,2-PG selectivity (%) |
| 21 | Cu—ZrO$_2$/MnO$_X$ | 5.5 | 50.7 | 83.5 |
| 21 | Cu—ZrO$_2$/MnO$_X$ | 12 | 62.3 | 79.6 |
| 12 | Cu—ZrO$_2$/MnO$_X$ | 12.5 | 62.6 | 90.3 |

Example 9

Ternary catalyst support materials or catalysts were prepared by co-precipitation methods. Table 9 listed two of the preparations in addition to Table 2. In a typical preparation, 267.7 g of 9.33 wt. % Mn(NO$_3$)$_2$ solution and 71.7 g of 13.8 wt. % Ni(NO$_3$)$_2$ solution was dissolved into 1400 g of ZrO(NO$_3$) solution (20 wt % ZrO$_2$) and precipitated with 25 wt % NaOH solution. The precipitation was conducted at a pH of 8.5. The precipitate was aged overnight and washed with excess de-ionized water until the conductivity of the final filtered water was less than 0.4 mS/cm. Then, the filtration cake was dried appropriately and then extruded. The extrudates were then dried at 110° C. for 3 h and calcination at 600° C. for 3 h with a heating ramp rate of 3 K/min.

Table 9 lists the basic physical properties of these materials. The pore volume varied from 0.3 to 0.5 mL/g. All the materials yielded surface area above 100 m²/g. When used as catalyst supports for hydrogenation/hydrogenolysis, Samples 13-14, showed increased mechanical strength.

TABLE 9

The properties of ternary catalyst support materials prepared by co-precipitation.

| Sample No. | composition wt. % (oxide basis) | Crush strength (lb/mm) | Pore volume (mL/g) | BET S.A (m²/g) | Attrition (%) | Calcination Temp. (° C.) |
|---|---|---|---|---|---|---|
| 13 | Mn 7%; Ni 3.0% | 2.50 | 0.48 | 132 | 1.8 | 600 |
| 14 | Mn 8%; Ni 6.0% | 3.18 | 0.35 | 108 | 0.6 | 600 |

It is understood that the examples and embodiments described herein are for illustrative purposes only. Unless clearly excluded by the context, all embodiments disclosed for one aspect of the invention can be combined with embodiments disclosed for other aspects of the invention, in any suitable combination. It will be apparent to those skilled in the art that various modifications and variations can be made to the present invention without departing from the scope of the invention. Thus, it is intended that the present invention cover the modifications and variations of this invention provided they come within the scope of the appended claims and their equivalents. All publications, patents, and patent applications cited herein are hereby incorporated herein by reference for all purposes.

We claim:

1. A catalyst material comprising
a catalyst support material comprising $ZrO_2$ and one or more oxides of manganese ($MnO_x$), the catalyst support material containing about 1 wt % to about 20 wt % of $MnO_x$, the total amount of $ZrO_2$ and $MnO_x$ being at least about 85 wt % of the catalyst support material, and
a catalyst metal disposed on the catalyst support material.

2. A catalyst material according to claim 1, wherein the the total amount of $ZrO_2$ and $MnO_x$ in the catalyst support material is at least about 95 wt %.

3. A catalyst material according to claim 1, wherein the weight ratio of $ZrO_2$ to $MnO_x$ in the catalyst support material is within the range of about 5:1 to about 25:1.

4. A catalyst material according to claim 1, wherein the catalyst support material further comprises one or more oxides of yttrium and/or lanthanum, wherein the molar ratio of the $ZrO_2$ to the oxides of yttrium and/or lanthanum is within the range of about 10:1 to about 100:1.

5. A catalyst material according to claim 1, wherein the catalyst support material has a pore volume within the range of about 0.1 to about 0.5 cm³/g.

6. A catalyst material according to claim 1, wherein the catalyst support material has a surface area within the range of about 10 to about 400 m²g.

7. A catalyst material according to claim 1, wherein the catalyst support material has crush strength within the range of about 45 N/cm to about 222 N/cm.

8. A catalyst material according to claim 1, wherein the catalyst support material is substantially free of any binder, extrusion aid or additional stabilizing agent.

9. A catalyst material according to claim, wherein the catalyst support material comprises 1 wt. % to 10 wt. % nickel oxide.

10. A catalyst material according to claim 1, wherein at least about 80 wt % of the $ZrO_2$ is in a tetragonal phase, and less than about 20 wt % of the $ZrO_2$ is in a monoclinic phase.

11. A catalyst material according to claim 1, wherein the $ZrO_2$ is in an amorphous phase.

12. A method for making a catalyst material according to claim 1, comprising extruding a zirconia/manganese oxide precursor material in the absence of any binder, extruding aid or additional stabilizing agent.

13. A catalyst material comprising a catalyst support material according to claim 1, and a catalyst disposed on the catalyst support material, wherein the catalyst metal comprises Ni, Cu, Co, Fe, Ru, Rh, Pd, Ag, Re, Os, Ir, Pt, Au, Bi, Sb, or a combination thereof.

14. A method for conducting a catalytic reaction comprising contacting one or more reactants with a catalyst material according to claim 1, wherein at least one of the reactants is in the aqueous phase, and wherein the reaction is conducted at a temperature within the range of 50 ° C. to 325 ° C., and a pressure within the range of about 10 bar to about 250 bar.

15. A method for converting a sugar, sugar alcohol or glycerol into a polyol or an alcohol comprising a shorter carbon-chain backbone, the method comprising contacting the sugar, sugar alcohol or glycerol with a catalyst material according to claim 1 and hydrogen.

16. A method according to claim 15, wherein the reaction is conducted at a temperature within the range of 50 ° C. to 325 ° C., and a pressure within the range of about 10 bar to about 250 bar.

17. A method according to claim 15, wherein converting the sugar, sugar alcohol or glycerol is achieved with at least 40% efficiency, and a total carbon atom selectivity of at least 70 mol %.

18. A method of hydrogenating an organic acid, the method comprising contacting organic acid with a catalyst material according to claim 13 and hydrogen.

19. A method according to claim 15, wherein the catalyst metal comprises Ni, Cu, Co, Fe, Ru, Rh, Pd, Ag, Re, Os, Ir, Pt, Au, Bi, Sb, or a combination thereof.

20. A method according to claim 15, wherein the catalyst metal is NiCu, NiSb, Ni, Cu, Ru, or NiCuBi.

21. A method according to claim 18, wherein the catalyst metal comprises Ni, Cu, Co, Fe, Ru, Rh, Pd, Ag, Re, Os, Ir, Pt, Au, Bi, Sb, or a combination thereof.

22. A catalyst material comprising a catalyst support material according to claim 1, wherein the catalyst metal NiCu, NiSb, Ni, Cu, Ru, or NiCuBi.

23. A catalyst material comprising a catalyst support material according to claim 1, wherein the catalyst support material contains about 1 wt % to about 15 wt % of $MnO_x$.

* * * * *